(12) United States Patent
Gerstel

(10) Patent No.: US 6,929,780 B2
(45) Date of Patent: Aug. 16, 2005

(54) VAPORIZER TUBE FOR VAPORIZING LIQUID SAMPLES IN CAPILLARY GAS CHROMATOGRAPHY

(75) Inventor: Joachim Gerstel, Mulheim a.d. Ruhr (DE)

(73) Assignee: Joint Analytical Systems GmbH, Mulheim a.d. Ruhr (DE)

( * ) Notice: Subject to any disclaimer, the term of this patent is extended or adjusted under 35 U.S.C. 154(b) by 249 days.

(21) Appl. No.: 10/197,633

(22) Filed: Jul. 16, 2002

(65) Prior Publication Data

US 2003/0017610 A1 Jan. 23, 2003

(30) Foreign Application Priority Data

Jul. 16, 2001 (DE) .......................................... 101 33 774

(51) Int. Cl.[7] ............................................. G01N 30/02
(52) U.S. Cl. ......................................................... 422/89
(58) Field of Search ...................... 422/89; 261/DIG. 56

(56) References Cited

U.S. PATENT DOCUMENTS 4,383,839 A * 5/1983 Sisti et al. ...................... 95/83
5,528,903 A * 6/1996 Schreckling ................. 60/736

* cited by examiner

Primary Examiner—Yelena G. Gakh
(74) Attorney, Agent, or Firm—Lawrence G Fridman

(57) ABSTRACT

The invention relates to a vaporizer tube for vaporizing liquid samples in capillary gas chromatography. The vaporizer tube is open throughout its whole length. It has throats which are shaped to provide, in their region, a heavy increase of the flow velocity of the carrier gas, which flows substantially unrestrictedly through the vaporizer tube. This increase of the flow velocity causes, in accordance with Bernoulli's law, reduction in pressure. Due to this pressure reduction, the easily volatile solvent is predominantly volatilized. This vaporized solvent is carried along by the carrier gas flow. The solvent can then be removed through an outlet of the sample inlet chamber. The sample proper is vaporized in the larger diameter, low velocity zones between the throats by heating the vaporizer tube and are fed to the capillary column, after the solvent has been volatilized. Thus the vaporizer tube with a plurality of throats acts like a multi-plate column.

8 Claims, 2 Drawing Sheets

VAPORIZER TUBE FOR VAPORIZING LIQUID SAMPLES IN CAPILLARY GAS CHROMATOGRAPHY

The invention relates to a vaporizer tube for vaporizing liquid samples in capillary gas chromatography.

BACKGROUND OF THE INVENTION

Gas chromatography is a method of separating substance mixtures. A sample of the substance mixture is vaporized. The vapor is "flushed", by means of an inert carrier gas flow, through a separating column filled with a separating substance. The various substances or components of the substance mixture will migrate through the separating column at different velocities, depending on their affinity to the separating substance such as the solubility in a liquid separating substance. The components of the sample fed to the inlet of the column together as a "plug", will appear at different times consecutively at the outlet of the column and will be detected by a detector responding to such components. When such component emerges from the column, the detector provides a "peak", i.e. for example, a tooth or bell shaped signal.

So-called "capillary" columns are a narrow tube the inner wall of which is coated by a usually liquid separating substance. In contrast thereto, so-called "packed" columns comprise a relatively wide tube which is filled with a granular separating substance or of granulates coated with a separating substance. Capillary columns provide high resolution, i.e. good separation of the various peaks. Capillary columns, however, can process small sample quantities only.

In order to be able to use sample quantities which can be handled easily, the sample is usually dissolved in an easily volatile solvent. This solvent should be volatilized and removed prior to the entering of the sample into the capillary column.

It is known (G. Schomburg, "Probenaufgabe in der Kapillargaschromatographie" in "LABO—Kennziffer-Fachzeitschrift für Labortechnik" July 1983) to dispense a liquid sample into a pre-separator in the form of a vaporizer tube filled with quartz wool. This vaporizer tube is surrounded by a programmable heater. The inlet end of the capillary column extends into the outlet end of the vaporizer tube.

Vaporizer tubes ("liners") are known, which have one or two spaced throats or reduced diameter sections. With these vaporizer tubes, plugs of glass or quartz wool or of a solid, granular separating substance are retained between the throats. The flow of sample liquid through the vaporizer tube is slowed down. The material retained between the throats acts like a packed separating column, through which a pre-separation of the sample is effected. At first, the easily volatile solvent will emerge from the outlet of the vaporizer tube, said solvent being removed by the carrier gas flow before the components of the sample proper are fed by the carrier gas flow to the inlet of the capillary column. Such a packed column as pre-separator delays the passage of the sample. In particular less volatile components are retained.

After sample feeding, the capillary column is subjected to a temperature program. At first, the temperature of the capillary column is low, whereby the migration velocity of all components of the sample is relatively low. This causes, at first, concentration of the sample within a rather short plug at the inlet of the capillary column, a so-called "focusing". When the temperature of the capillary column is subsequently raised, the various components are transported by the carrier gas flow through the capillary column at different velocities. Such focusing is impeded by packed columns as pre-separators.

DISCLOSURE OF THE INVENTION

It is an object of the invention to improve the volatilization of samples in a device of the type discussed above.

It is a more specific object of the invention to volatilize and remove the solvent without impeding the focusing of the sample proper at the inlet of a capillary column.

To this end, the vaporizer tube is open throughout its whole length for the passage of the sample and of a carrier gas flow. The vaporizer tube has throat means, which are so designed as to heavily increase the flow velocity therein and, thereby, generating reduced pressure.

According to the invention, the throat or throats of the vaporizer tube do not serve to retain a packing of quartz wool or the like. Rather is such packing intentionally avoided, and the vaporizer tube is open throughout its whole length. The throats are designed such that a strong increase of the flow velocity of the carrier gas is achieved, the carrier gas flowing unrestrictedly through the vaporizer tube. Such an increase of the flow velocity at the throats does not occur in the prior art vaporizer tubes because of the packing. According to Bernoullie's law, this increase in the flow velocity causes reduced pressure. Because of this reduced pressure, the easily volatile solvent will be vaporized predominantly. This vaporized solvent is carried along by the carrier gas. The solvent can then be removed through an outlet of a sample inlet chamber. The sample proper is vaporized in the larger diameter lower velocity zones between the throats by heating the vaporizer tube and is fed to the capillary column, after the solvent has been volatilized and removed. The vaporizer tube acts like a multi-plate column.

According to another aspect of the invention, a method of vaporizing liquid samples dissolved in an easily volatile solvent for the capillary gas chromatography in a heated vaporizer tube, to which the sample with the solvent is fed and through which the sample and solvent is transported by means of a carrier gas flow, comprises the steps of: transporting the sample and the carrier gas flow through a free passage of the vaporizer tube; generating an increased flow velocity and, thereby, reduced pressure at selected locations of the vaporizing tube, such that predominantly easily volatile solvent is volatilized by the reduced pressure, removing the vaporized solvent by the carrier gas flow, thermally vaporizing the sample, after the solvent has been substantially volatilized, and transporting the vaporized sample to a gas chromatographic capillary column by means of the carrier gas flow.

Further objects and features of the invention will be apparent to those skilled in the art from the following detailed description of preferred embodiments of the invention.

Embodiments of the invention are described below with reference to the accompanying drawings.

PREFERRED EMBODIMENTS OF THE INVENTION

Figure 1:
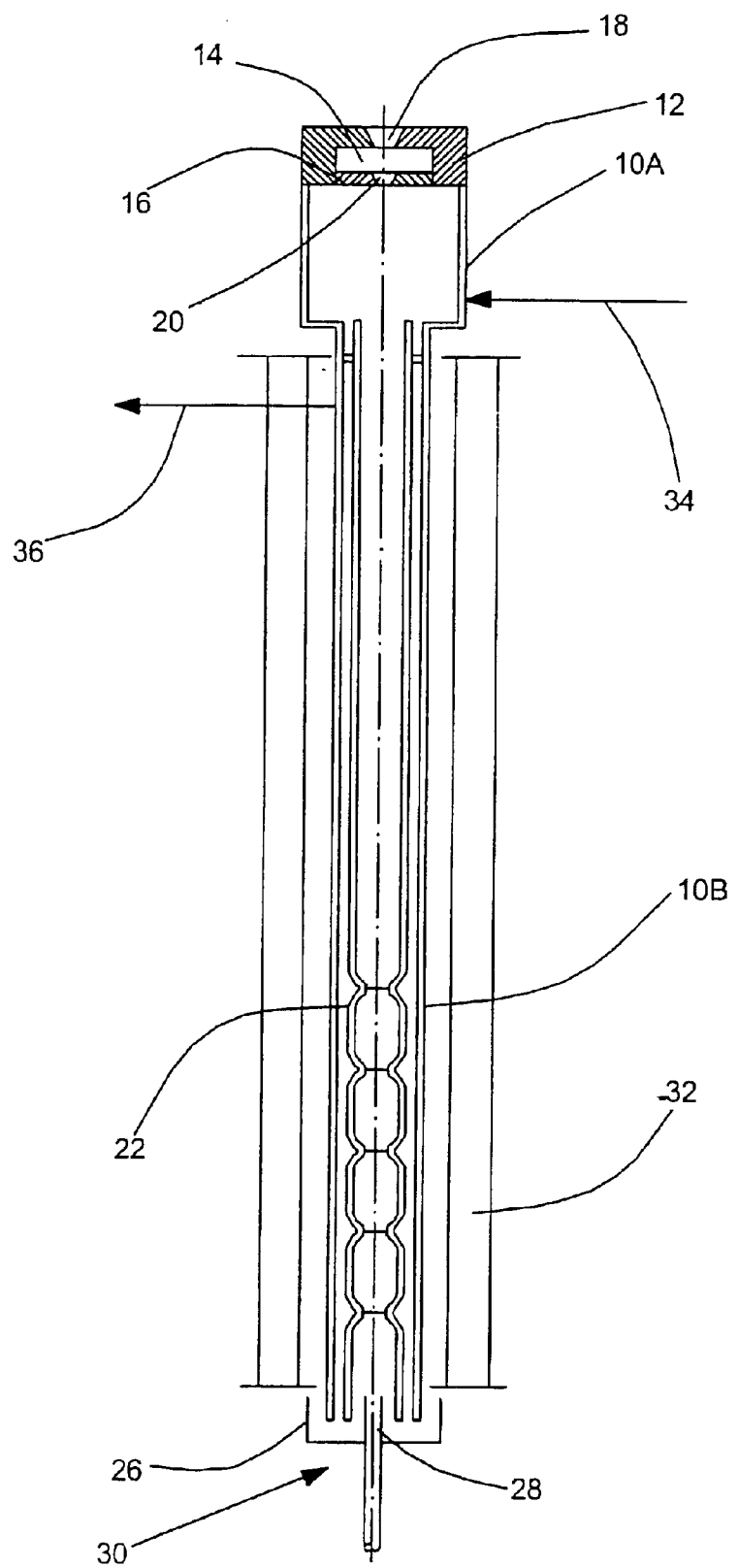
FIG. 1 schematically shows a device for sample feeding in capillary gas chromatography comprising a vaporizer tube, which is provided with throats.

Referring to FIG. 1, numeral 10 designates a sample inlet chamber. The sample inlet chamber 10 is closed at its upper end by a cap 12, which holds a septum 14. The septum 14 is supported by a plate 16. The cap 12 has a conical aperture 18 tapering towards the septum. The plate 16 has an aperture 20 aligned with the aperture 18 and tapering towards the bottom of FIG. 1. The sample inlet chamber 10 has a larger diameter, cylindrical upper portion 10A and an adjacent lower portion 10B of reduced diameter.

Figure 2:
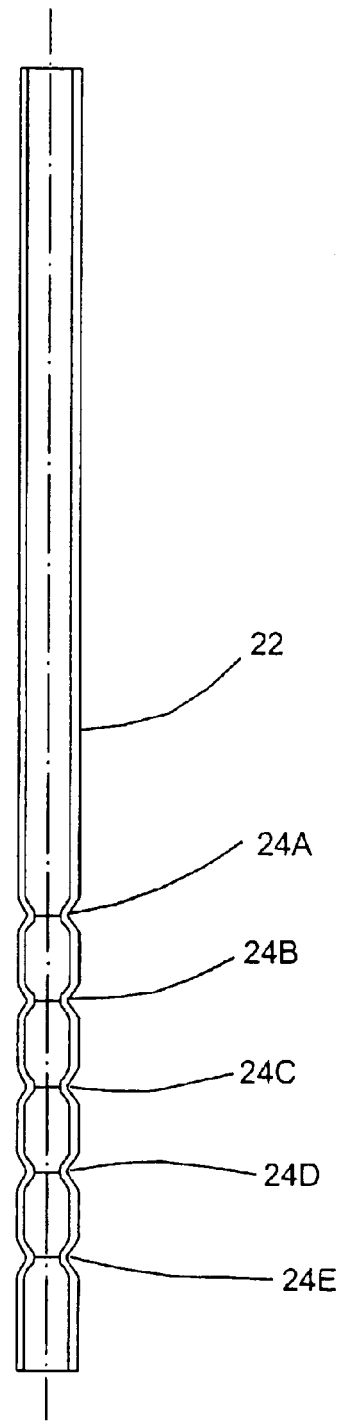
FIG. 2 shows the vaporizer tube in the device of FIG. 1.

A vaporizer tube 22 is retained coaxial in the sample inlet chamber. The vaporizer tube 22 is shown in detail in FIG. 2. The vaporizer tube 22 consists of an inert material such as glass or quartz. The vaporizer tube 22 has a sequence of equally spaced throats 24A, 24B, 24C, 24D and 24E. Each of the throats is shaped like a Venturi tube. In the region of each of the throats, the flow velocity of the medium flowing through the vaporizer tube is substantially increased. According to Bernoulli's law, a reduction of pressure is caused thereby. In a preferred embodiment, the internal diameter of the vaporizer tube is 3 mm, while the narrowest spot of the Venturi structure of the throat has an inner diameter of 1 mm. A jacket-shaped annular chamber is defined between the outer surface of the vaporizer tube 22 and the inner surface of the narrower portion 10B of the sample inlet chamber 10.

A connector 26 in the form of a cap nut is placed on the lower end of the sample inlet chamber 10. This connector carries centrally the inlet end of a capillary column 30.

The sample inlet chamber 10 is heated by a programmable heater 32.

Numeral 34 designates a carrier gas inlet. Numeral 36 designates a "split" outlet, through which the volatilized solvent can emerge.

The described sample inlet device operates as follows:

A well-defined quantity of a liquid sample consisting of a substance mixture and an easily volatile solvent is injected into the vaporizer tube 22 by means of a syringe. To this end, the needle of the syringe is pierced through the septum 14. The needle is guided by the tapering apertures 18 and 20. Carrier gas is directed into the vaporizer tube through a carrier gas inlet at the upper end thereof.

In the regions of the throats 24A to 24E, the open cross sectional area is reduced heavily, about by a factor of 10, and the flow velocity is increased accordingly. This results in reduced pressure in these areas. Due to this pressure reduction, predominantly the easily volatile solvent of the sample passing through the vaporizer tube is volatilized. The thus volatilized solvent is carried along by the carrier gas flow and, through the annular chamber between vaporizer tube 22 and inner surface of the sample inlet chamber 10, gets to the "split" outlet 36, which is open, at first.

Then the slit optlet 36 is closed, whereby the carrier gas flow now flows through the capillary column 30. The vaporizer tube is heated by the heater 32. The sample proper is now carried by the carrier gas to the inlet of the capillary column 30. By the temperature programming, the will be "focusing" of the sample, as described above, and then a separation of the components on their way through the capillary column 30.

Figure 3:
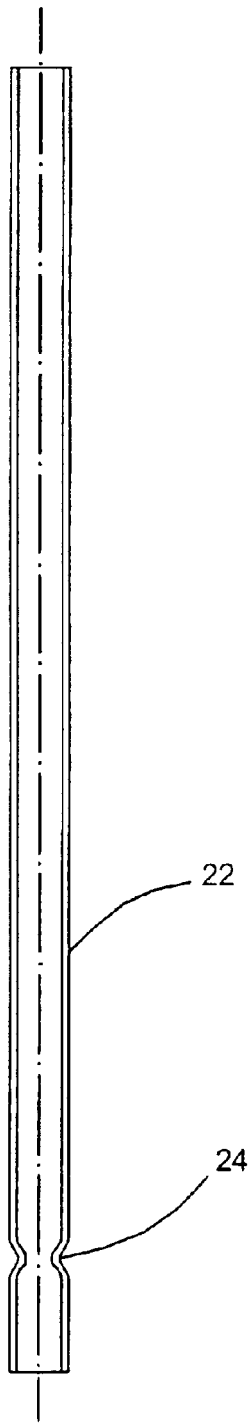
FIG. 3 shows a modified embodiment of the vaporizer tube having one single throat.

FIG. 3 shows a vaporizer tube 22 with one single throat 24.

I claim:

1. A sample inlet and vaporizing device arrangement for capillary gas chromatography, comprising:

a sample inlet chamber having an inlet-side first portion and an elongated outlet-side second portion, injection means for injection of liquid samples with easily volatile solvent into said first portion and means for supplying a carrier gas into said first portion, heating means for heating said second portion of said sample inlet chamber, a vaporizer tube for vaporizing said liquid samples, said vaporizer tube having an inlet end and an outlet end, extending longitudinally within said second portion of said inlet chamber and defining a longitudinal passage which is open along its whole length for the passage of a sample to be subjected to gas chromatography and of a carrier gas flow, said inlet end communicating with said first portion of said sample inlet chamber said passage formed with a passage area and throat means having a Venturi tube-type configuration for increasing the flow velocity of said carrier gas flow to provide reduced pressure in said throat means, so as to enhance vaporization of said volatile solvent, split outlet means at said second portion of said sample inlet chamber, and means for holding an inlet end of a capillary column to extend into said outlet end of said vaporizing tube.

2. An arrangement as claimed in claim 1, wherein throat means comprise a plurality of throats spaced along a length of said vaporizer tube.

3. An arrangement as claimed in claim 2, wherein said throat means comprises more than two throats.

4. An arrangement as claimed in claim 3, wherein said throats are equally spaced.

5. An arrangement as claimed in claim 4, wherein said throats cause reduction of the free cross section of said vaporizer tube by a factor of at least 1.8.

6. A sample inlet and vaporizing device arrangement for capillary gas chromatography, comprising:

a sample inlet chamber having an inlet-side first portion and an elongated outlet-side second portion, injection means for injection of liquid samples with easily volatile solvent into said first portion, means for supplying a carrier gas into said first portion, heating means for heating said second portion of said sample inlet chamber, a vaporizer tube for vaporizing said liquid samples, said vaporizer tube having an inlet end and an outlet end extending longitudinally within said second portion of said inlet chamber and defining a longitudinal passage which is open along entire length thereof for the passage of a sample to be subjected to gas chromatography and of a carrier gas flow, said inlet end communicating with said first portion of said sample inlet chamber, said passage being formed with multiple passage areas and throat means having a Venturi tube-type configuration for increasing the velocity of said carrier gas flow, so as to provide reduced pressure in said multiple passage cross-sectional areas and throat means.

7. An arrangement as claimed in claim 6, wherein said multiple passage areas and throat means comprise at least two throats.

8. An arrangement as claimed in claim 7, wherein said throats are equally spaced from each other.

* * * * *